United States Patent [19]

Birkenmeyer

[11] 4,310,660

[45] Jan. 12, 1982

[54] LINCOMYCIN COMPOUNDS

[75] Inventor: Robert D. Birkenmeyer, Comstock Township, Kalamazoo County, Mich.

[73] Assignee: The Upjohn Company, Kalamazoo, Mich.

[21] Appl. No.: 194,634

[22] Filed: Oct. 6, 1980

Related U.S. Application Data

[60] Division of Ser. No. 148,056, May 19, 1980, Pat. No. 4,278,789, which is a continuation-in-part of Ser. No. 96,652, Nov. 23, 1979, abandoned.

[51] Int. Cl.$^3$ .............................................. C07H 15/16
[52] U.S. Cl. ...................................... 536/11; 424/180
[58] Field of Search ......................................... 536/11

[56] References Cited

U.S. PATENT DOCUMENTS

| | | | |
|---|---|---|---|
| 3,086,912 | 4/1963 | Bergy et al. | 536/11 |
| 3,496,163 | 2/1970 | Birkenmeyer et al. | 536/11 |
| 3,849,396 | 11/1974 | Birkenmeyer et al. | 536/11 |
| 3,856,943 | 12/1974 | Birkenmeyer et al. | 536/11 |

*Primary Examiner*—Johnnie R. Brown
*Attorney, Agent, or Firm*—Roman Saliwanchik

[57] ABSTRACT

Novel useful analogs of the well known antibiotics lincomycin and clindamycin. These analogs are prepared by condensing a cyclic acid with a sugar amine.

3 Claims, No Drawings

LINCOMYCIN COMPOUNDS

DESCRIPTION

Cross Reference to Related Application

This is a division of application Ser. No. 148,056, filed May 19, 1980, now U.S. Pat. No. 4,278,789, which is a continuation-in-part of Ser. No. 096,652, filed Nov. 23, 1979, now abandoned.

BACKGROUND OF THE INVENTION

The characteristics and preparation of the antibiotic lincomycin are disclosed in U.S. Patent 3,086,912. Clindamycin is disclosed in U.S. Patent 3,496,163. These antibiotics have been extensively used as medicines in humans and animals. A number of patents world-wide have issued concerning these antibiotics and a variety of derivatives thereof.

Lincomycin has the following structural formula

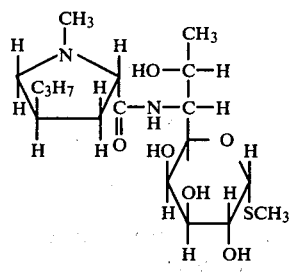

Clindamycin has the following structural formula

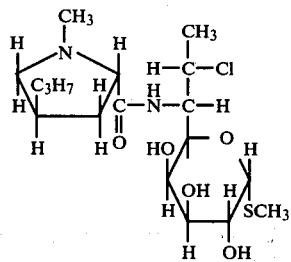

BRIEF SUMMARY OF THE INVENTION

This application relates to novel and useful compounds of the formula:

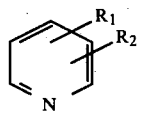

wherein $R_1$, which can be singly or multiply substituted in any position of the pyridine ring not already substituted by $R_2$, is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, $-(CH_2)_n-OH$, $-(CH_2)_n-NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof, wherein $R_2$, which can be singly substituted in any position of the pyridine ring not already substituted by $R_1$, is

and X is the amino function of a compound selected from the group consisting of 7(R)-hydroxy-methyl 1-thio-α-lincosaminide, 7(S)-hydroxy-methyl 1-thio-α-lincosaminide, 7(S)-halo-methyl 1-thio-α-lincosaminide, 7(R)-halo-methyl 1-thio-α-lincosaminide, 7(S)-methoxy-methyl 1-thio-α-lincosamide, 7-deoxy-7(S)-(methylthio)-methyl 1-thio-α-lincosaminide, 7-deoxy-7(S)-(2-hydroxyethylthio)methyl 1-thio-α-lincosaminide, and 7-deoxy-7(S)-(3-hydroxypropylthio)-methyl 1-thio-α-lincosaminide; and the pharmaceutically acceptable acid addition salts thereof, and to novel compounds of the formula:

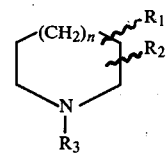

wherein $R_1$ can be singly or multiply substituted in the ring on the same or different carbons, and $R_2$, which can be in the 2, 3, 4, 5, 6, 7, 8 or 9 position of the ring, are as defined above; wherein $R_3$ is selected from the group consisting of H, $CH_3$, $C_2H_5$, and $-CH_2-CH_2-OH$; wherein n is an integer of from 1 to 4, inclusive; and the pharmaceutically acceptable acid addition salts thereof.

Compounds of particular importance are of the formula:

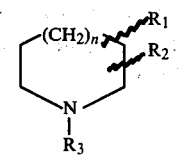

wherein $R_1$ is in the 4 position and is alkyl of from 1 to 8 carbon atoms, inclusive, and isomeric forms thereof; wherein $R_3$ is as defined above; wherein $R_2$ is in the 2 or 3 position and is otherwise as defined above; wherein n is 1; and the pharmaceutically acceptable acid addition salts thereof.

Important precursor compounds of the above have the formula

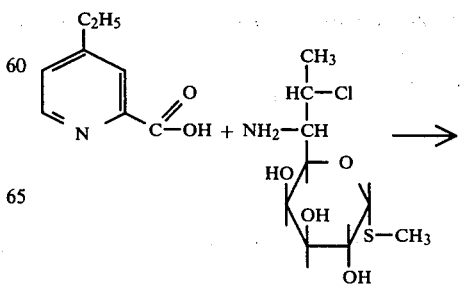

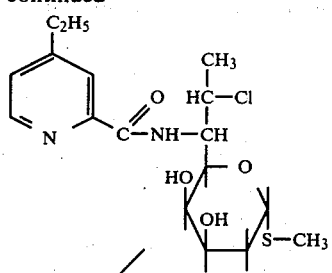

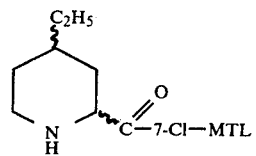

has been shown to be 5 to 10 times more active than clindamycin against *S. aureus* and *S. hemolyticus* in laboratory mice.

An isomer of V may be isolated from the above reaction and is presumed to be the D-cis compound, VA. The D-cis structure is not as potent an antibacterial agent as the L-cis compound.

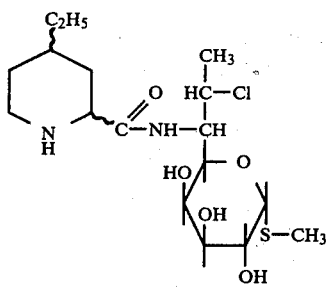

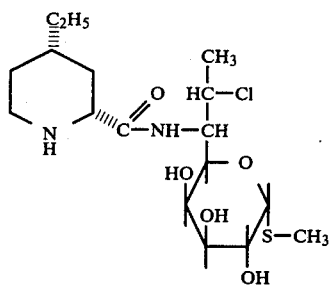

wherein $R_1$ and $R_2$ are as defined immediately above.

The synthesis of the novel analogs described herein can be shown in exemplary form as follows:

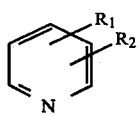
IV

Also within the scope of the subject invention are compounds of the formulae

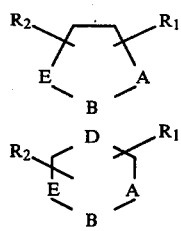
VI

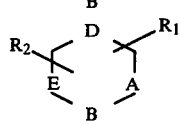
VII

The wavy lines denote either the D-cis or L-cis isomer.

An alternate procedure which may be used to synthesize the novel analogs described herein can be shown in exemplary form as follows:

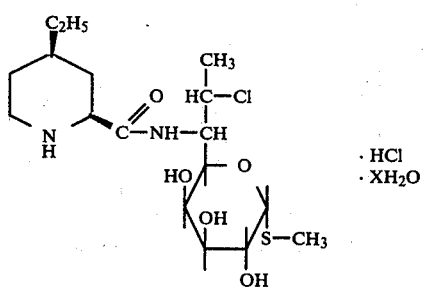
V wherein A, B, D and E are selected from the group consisting of nitrogen, oxygen, sulfur and $CR_1R_1$; $R_1$ and $R_2$ are as defined previously and can be attached to any ring carbon or nitrogen atom; $R_1$ can be multiply attached to any ring carbon atom, and the pharmaceutically acceptable acid addition salts thereof.

Further, this application relates to novel 2-phosphates and 2-palmitates wherein the substitution is attached to the oxygen atom at the 2 position of the sugar ring of the above compounds.

DETAILED DESCRIPTION OF THE INVENTION

Upon reacting an amino acid of the formula

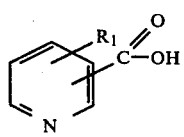

The wavy line denotes either the D-cis, L-cis, D-trans or L-trans structures.

The L-cis structure

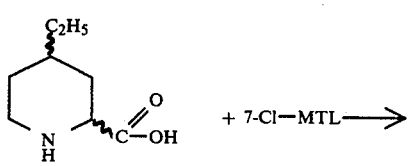

wherein $R_1$, which can be singly or multiply substituted in any position of the pyridine ring not already substituted by

is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl and substituted phenyl; —(CH$_2$)$_n$—OH, —(CH$_2$)$_n$—NR$_4$R$_5$, and isomeric forms thereof, wherein n is an integer of from 1 to 8, inclusive, R$_4$ and R$_5$ are H or alkyl of from 1 to 8 carbon atoms, inclusive, and isomeric forms thereof, wherein

which can be singly substituted in any position of the pyridine ring not already substituted by R$_1$, with a sugar amine compound selected from the group consisting of 7(R)-hydroxy-methyl 1-thio-α-lincosaminide, 7(S)-hydroxy-methyl 1-thio-α-lincosaminide, 7(S)-halo-methyl 1-thio-α-lincosaminide, 7(R)-halo-methyl 1-thio-α-lincosaminide, 7(S)-methoxy-methyl 1-thio-α-lincosaminide, 7-deoxy-7(S)-(methylthio)-methyl 1-thio-α-lincosaminide, 7-deoxy-7(S)-(2-hydroxyethylthio)-methyl 1-thio-α-lincosaminide, and 7-deoxy-7(S)-(3-hydroxypropylthio)-methyl 1-thio-α-lincosaminide; there are obtained novel and useful compounds of formula I.

Upon reacting an amino acid of the formula

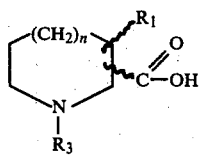

wherein R$_1$ and the position of substitution of

are as defined above; wherein R$_3$ is selected from the group consisting of H, CH$_3$, C$_2$H$_5$, and —CH$_2$—CH$_2$—OH; wherein n is an integer of from 1 to 4, inclusive, with a sugar amine compound, as defined above, there are obtained novel and useful compounds of formula II.

Upon reacting an acid of the formulae

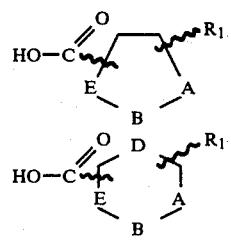

wherein A, B, D and E are selected from the group consisting of nitrogen, oxygen, sulfur and CR$_1$R$_1$; R$_1$ is as defined previously and can be attached to any ring carbon or nitrogen atom; R$_1$ can be multiply attached to any ring carbon atom;

can be attached to any ring carbon or nitrogen atom, with a sugar amine compound selected from the group as defined above, there are obtained novel and useful compounds of formulae VI and VII.

MTL is methyl 1-thio-α-lincosaminide of the formula

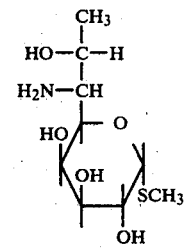

epi-MTL is methyl 7(S)-7-deoxy-7-hydroxy-1-thio-α-lincosaminide of the formula

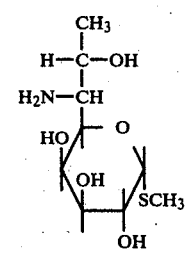

7-Cl-MTL is methyl 7(S)-7-deoxy-7-chloro-1-thio-60-lincosaminide of the formula

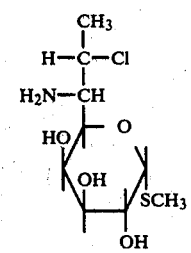

epi-7-Cl-MTL is methyl 7(R)-7-deoxy-7-chloro-1-thio-α-lincosaminide of the formula

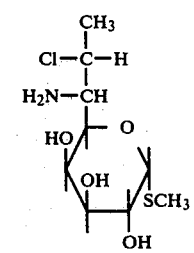

7(S)-methoxy-methyl 1-thio-α-lincosaminide can be shown as follows (See U.S. Pat. No. 3,702,322, Example 1, Part B-1):

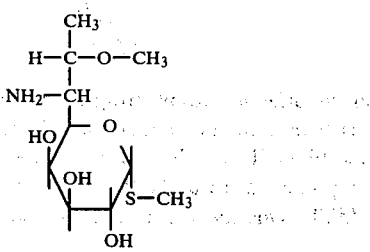

With reference to the following formula, 7-deoxy-7(S)-(methylthio)-methyl 1-thio-α-lincosaminide exists when R is $CH_3$; 7-deoxy-7(S)-(2-hydroxyethylthio)-methyl 1-thio-α-lincosaminide exists when R is $-CH_2-CH_2-OH$; and, 7-deoxy-7(S)-(3-hydroxypropylthio)-methyl 1-thio-α-lincosaminide exists when R is $-CH_2-CH_2-CH_2-OH$ (See U.S. Pat. No. 3,915,954, Examples 1, 10 and 31):

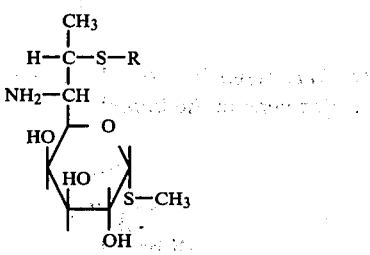

The hydroxy and halo groups at the 7 position of the above formulas can be shown as follows

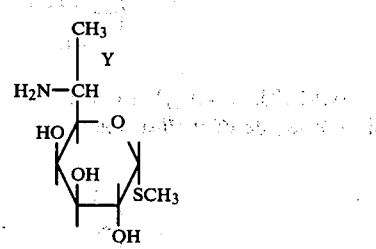

wherein Y is selected from the group consisting of 7(R)-hydroxy, 7(S)-hydroxy, 7(S)-halo, and 7(R)-halo.

When a pyridine acyl group is used, the resulting analog can be reduced to give a mixture of the corresponding saturated compounds, one of which is the L-cis isomer. Other compounds which may be present include the L-trans, D-cis, and D-trans isomers. Generally, for any of the compounds described herein, the reduced form is more antibacterially-active than the unsaturated precursor. The use of a piperidine acyl group gives analogs existing as D-cis, L-cis, D-trans, and L-trans isomers. Again, the L-cis isomer has been found to be more anti-bacterially active.

The general method used herein to prepare the novel analogs is the well known process wherein an appropriate acid is coupled with an appropriate sugar amine. ("Mixed Carboxylic Acid Anhydride Procedure," Chemistry of The Amino Acids, Vol. 2, p. 970, John Wiley and Sons, Inc. 1961). When the acid is unsaturated, the resulting unsaturated analog can be catalytically reduced under standard conditions to prepare the saturated analog. For example, the reduction can be conducted using the following conditions:

$H_2$ at 5 to 50 psi
Catalyst—platinium oxide ($PtO_2$)
Solvent—$H_2O$ or $H_2O+MeOH$, or $H_2O+EtOH$
HCl—10% excess
Time—24 to 48 hours As used herein, alkyl of 1 to 8 carbon atoms, inclusive, and isomeric forms thereof, includes methyl, ethyl, propyl, butyl, pentyl, hexyl, heptyl, octyl, and branched chain isomers thereof.

Substituted alkyl means the above alkyl compounds in which one or more of the hydrogen atoms has been replaced by a halogen, i.e., Cl, Br, F, and I, oxygen, hydroxyl, amine (primary), amine (secondary-alkyl substituted by alkyl as above), amine (tertiary-alkyl substituted by alkyl as above), sulfur, —SH, and phenyl. Exemplary compounds are 1-fluoroethyl, 1-chloroethyl, 2-fluoroethyl, 2-chloroethyl, 1-bromopropyl, 2-iodopropyl, 1-chlorobutyl, 4-fluorobutyl, and 4-chlorobutyl.

Cycloalkyl means cyclopropyl, cyclobutyl, cyclopentyl, cyclohexyl, cycloheptyl and cyclooctyl.

Substituted cycloalkyl means a cycloalkyl substituted as above for substituted alkyl. Exemplary compounds are 2-cyclopropylethyl, 3-cyclobutylpropyl, 4-cyclopentylbutyl, and 4-cyclohexylbutyl.

Aromatic means phenyl and substituted phenyl wherein one or more of the hydrogen atoms has been replaced by a halogen, as above, hydroxyl, amine (primary, secondary, and tertiary with the latter two alkyl substituted as above), —SH, and phenyl. Exemplary compounds are p-bromophenyl, m-iodophenyl, o-chlorophenyl, p-ethylphenyl, m-propylphenyl, o-methylphenyl, and p-octylphenyl.

As detailed infra, the compounds of the invention can be phosphorylated to give the 2-phosphate, and acylated to give the 2-palmitate which are both anti-bacterially-active in vivo.

Substituted oxygen means oxygen substituted by an alkyl of from 1 to 8 carbons, inclusive, aryl, and substituted aryl.

Substituted nitrogen means nitrogen substituted by an acyl of from 2 to 18 carbons, a monoalkyl of 1–8 carbons, inclusive, and a dialkyl, wherein the alkyl is from 1 to 8 carbons, inclusive, including the isomeric forms for all acyl and alkyl groups.

Halo means chloro, bromo, iodo, or fluoro.

Exemplary sources for the amino acids used as starting materials herein are as follows:

1. Heterocyclic Compounds: Vol. 1, John Wiley and Sons, Inc., 1950. This source describes the preparation of halogen and alkyl substituted amino acids.

2. Chem. Abstracts:

| | |
|---|---|
| 81 - 105223A | - alkyl and cycloalkyl |
| 81 - 152243S | - alkyl and halogen substituted |
| 82 - 170746H | - halogen substituted |
| 85 - 46322Q | - dihalo substituted |
| 85 - 177258W | - dihalo substituted |
| 84 - 116928X | - dihalo substituted |
| 81 - 3737d | - phenyl substituted |
| 78 - 58201t | - phenyl substituted |
| 76 - 126800y | - tetrahalo substituted |
| 82 - 11036K | - bromo substituted |
| 83 - 27119W | - bromo substituted |
| 84 - 16613X | - bromo substituted |
| 78 - 123494G | - bromo substituted |

-continued

| Ref | Compound |
|---|---|
| 84 - 135488V - | 5-(3-bromobut-2-enyl)pyridine-2-carboxylic acid (CH₂CH₂C(Br)=CH—CH₃ substituent) |
| 81 - 151951J - | 5-methoxy-6-bromopyridine-2-carboxylic acid |
| 81 - 77809a - | 5-(bromomethyl)pyridine-2-carboxylic acid |
| 84 - 30918G - | 5-pentyl-4-methoxypyridine-2-carboxylic acid |
| 81 - 33139C - | 3,5-diethoxypyridine-2-carboxylic acid |
| 79 - 19109V - | 5-iodopyridine-2-carboxylic acid |
| 81 - 3737D - | 4-phenoxypyridine-2-carboxylic acid |
| 81 - 135946K - | 6-(cyclopentenyloxy)pyridine-2-carboxylic acid |
| 85 - 177349B - | 4-acetamidopyridine-3-carboxylic acid |
| 78 - 71865G - | 6-chloro-4-ethoxypyridine-3-carboxylic acid |
| 81 - 135964K - | 6-(3-chlorophenoxy)pyridine-3-carboxylic acid |
| 83 - 147397G - | 2-dimethylamino-6-chloropyridine-4-carboxylic acid |
| 82 - 11036K - | 3-amino-4-methylpyridine-2-carboxylic acid |
| 84 - 116928X - | 3,6-dichloropyridine-2-carboxylic acid |
| 81 - 33139C - | 3,5-diethoxypyridine-2-carboxylic acid |
| 76 - 126800Y - | 3,4,5,6-tetrachloropyridine-2-carboxylic acid |
| 79 - 115449b - | 5-pentyl-4-ethoxypyridine-2-carboxylic acid |
| 67 - 63229K - | 3,5-dichloro-4-methylaminopyridine-2-carboxylic acid |
| 68 - 104926b | 4,6-dimethylpyridine-2-carboxylic acid |
| 69 - 59048Z | 5-methyl-4-phenylpyridine-2-carboxylic acid |
| 71 - 124907M | hexahydropyridazine-3-carboxylic acid and 5-hydroxy derivative |
| 68 - 59465N | methyl 3,6-dihydro-2H-1,2-oxazine-3-carboxylate |

This compound can be hydrolyzed to the acid by means well known in the art, which acid can then be reduced, also by means well known in the art.

86 - 106501e 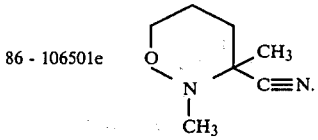

This compound can be hydrolyzed to the acid by means well known in the art. The resulting acid then can be N-demethylated by the procedures disclosed in U.S. Pat. No. 3,583,972.

69 - 67282M 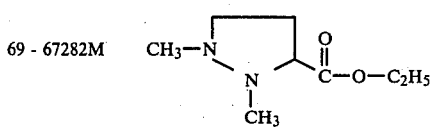

This compound can be hydrolyzed to the acid by means well known in the art.

90 - 70297-14-Z 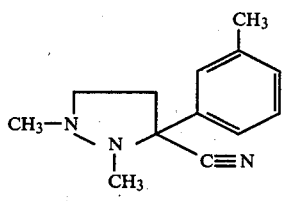

This compound can be hydrolyzed to the acid by means well known in the art. Also, one or both of the N-CH$_3$ groups can be removed from the resulting acid by following the procedures disclosed in U.S. Pat. No. 3,583,972.

90 - 168488X 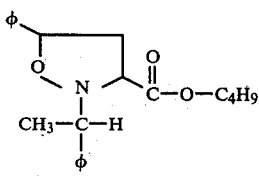

This compound can be hydrolyzed to the acid by means well known in the art. The resulting acid can be converted to the following compound

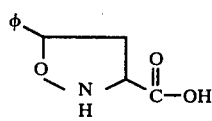

by methods disclosed in U.S. Pat. No. 3,583,972.

85 - 142995G 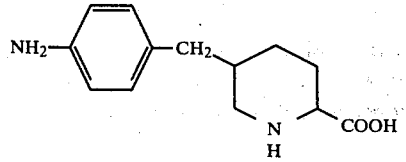

81 - 15202S 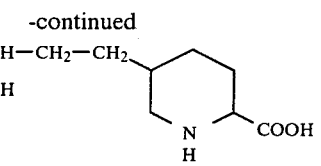

75 - 110156M 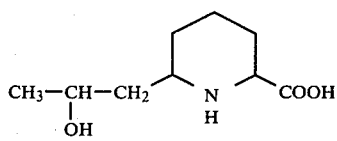

Compounds having free NH$_2$ or OH groups will have to have these groups protected before being condensed with the amino sugar. Protection of such groups is well known in the art. See Protective Groups in Organic Chemistry, J. F. W. McOmie, Plenum Publishing Co., Ltd., 1973.

3. Jour. Chem. Soc. 1969-2134: Various H-alkyl substituted pyridines

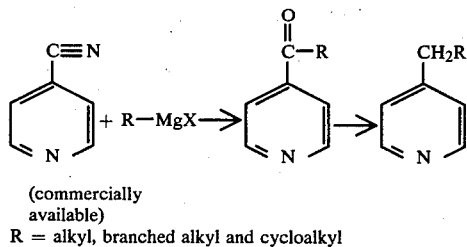

(commercially available)
R = alkyl, branched alkyl and cycloalkyl

4. Jour. Chem. Soc. 1969-934:

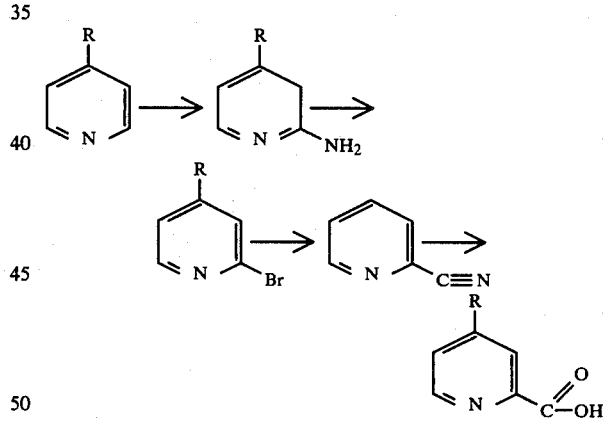

The following examples are illustrative of the process and products of the invention, but are not to be construed as limiting. All percentages are by weight and all solvent mixture proportions are by volume unless otherwise noted.

EXAMPLE 1

4-Cis-ethyl-1-pipecolic acid amide of 7-Cl-MTL.HCl (U-57,930E-Compound V)

Part I

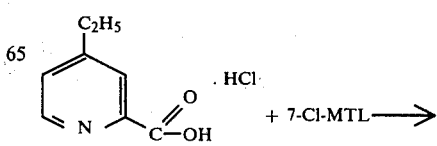

-continued

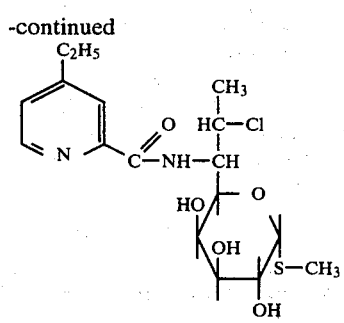

A solution of 67 g (0.357 moles) of the amino acid HCl (C.A. 51, 1643a, 1957) and 71.5 g (0.714 moles) of triethylamine dissolved in 2.5 liters of acetonitrile is cooled to 10° C. and 47.6 g (0.354 moles) of isobutyl-chloroformate added in one portion. This mixture (Solution A) is stirred at 10° C. for 1 hour. Solution B is made up by dissolving 97.7 g (0.357 moles) of 7-Cl-MTL (J. Med. Chem., 12-780, 1969, B. J. Magerlein and F. Kagan) in a warm mixture of 1500 ml of acetone and 1500 ml of H₂O. Solution B is cooled to 30° C. and added in one portion to Solution A. The reaction is stirred at 25° C. for 18 hours and the acetone and acetonitrile removed under vacuum. The white, mushy residue is filtered and the crystalline material collected and dried to give 95 g of pure product. Workup of the filtrate (chromatography) gave another 10 g of product. The overall yield is 73%.

Anal. Calcd. for $C_{17}H_{25}ClN_2O_5S$: C, 50.42; H, 6.22; N, 6.92; S, 7.92; Cl, 8.76. Found: C, 50.67; H, 6.40; N, 6.64; S, 7.90; Cl, 8.70. $\alpha_D^{CHCl_3}$ (C, 1.0)+293°.

PART II

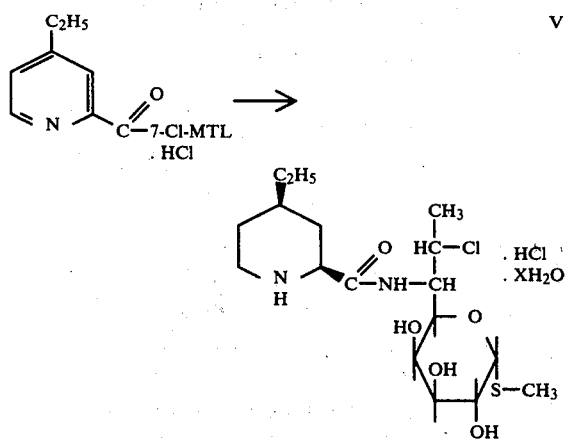

A mixture of 4.05 g (0.01 mole) of starting material, 40 ml of water, 60 ml of methanol, 1.0 ml of 37% HCl and 8.0 g of PTO₂ catalyst were reduced on a Parr hydrogenator at 50 p.s.i. for 3 hours. Analysis of the reaction mixture by TLC on silica gel plates in a system composed of CHCl₃:methanol (6:1) showed that all of the starting material was gone and that two more polar materials were present in a ratio of about 1:1. The reaction was filtered to remove the catalyst and the filtrate concentrated under vacuum to give a white crystalline mush. This was filtered and the filtrate saved. The white solid, which was the most polar of the two products observed upon TLC of the reduction mixture, was recrystallized from water to give the desired product, U-57,930E, m.p. 222°–224°, in a yield of from 25 to 35%.

Anal. Calcd. for $C_{17}H_{32}Cl_2N_2O_5S$: C, 45.63; H, 7.21; N, 6.26; S, 7.17; Cl, 15.85. Found: C, 45.77; H, 7.44; N, 6.39; S, 7.21; Cl, 16.17. $\alpha_D^{H_2O}$ (C, 1.0)+176°.

The absolute configuration and sterochemistry of V was established by X-ray crystallography.

U-57,930E, tested in comparison with clindamycin, has the following antimicrobial spectra:

TABLE I

The Minimal Inhibitory Concentration of U-57,930E and Clindamycin Vs. Aerobic Bacteria.

| Organism | UC | MIC (μg/ml) Clindamycin | MIC (μg/ml) U-57,930E |
|---|---|---|---|
| Staphylococcus | 6685 | >25 | >25 |
| aureus | 6686 | .05 | .20 |
|  | 6687 | .025 | .20 |
|  | 6688 | >25 | >25 |
|  | 6689 | .05 | .78 |
|  | 6690 | .025 | .20 |
|  | 6691 | .10 | .20 |
|  | 6692 | >25 | >25 |
|  | 6693 | .05 | .78 |
|  | 6694 | >25 | >25 |
|  | 6695 | .10 | .39 |
|  | 6696 | .10 | .39 |
|  | 6675 | .05 | .39 |
|  | 76 | .05 | .10 |
|  | 746 | <.05 | .05 |
|  | 571 | .20 | .78 |
|  | 570 | .20 | .39 |
| Staphylococcus | 719 | .10 | .20 |
| epidermidis | 3389 | .10 | .20 |
| Streptococcus faecalis | 694 | 25 | 6.25 |
| Streptococcus pyogenes | 152 | ≦.012 | ≦.012 |
| Streptococcus viridans | 153 | ≦.012 | .05 |
|  | 871 | ≦.012 | ≦.012 |
| Diplococcus pneumoniae I | 41 | ≦.012 | ≦.012 |
| Diplococcus pneumoniae II | 3213 | ≦.012 | ≦.012 |
| Escherichia coli | 45 | 50 | >50 |
| Proteus vulgaris | 93 | >50 | >50 |
| Klebsiella pneumoniae | 58 | 6.25 | >50 |
| Salmonella schottmuelleri | 126 | >50 | >50 |
| Pseudomonas aeruginosa | 95 | >50 | >50 |

The procedure for the above test is as follows:

The Minimal Inhibitory Concentration (MIC's) of both compounds Vs. aerobic bacteria is determined using a standard microplate broth-dilution method. Brain Heart Infusion (BHI-Difco) broth medium is used, and the plates are incubated at 37° C. for 20 hrs.

*S. aureus* UC 6685–6696 are clinical isolates which are resistant to one or more commercial antibiotics. "UC" is a registered trademark of The Upjohn Company Culture Collection. These cultures can be obtained from The Upjohn Company in Kalamazoo, Mich., upon request.

TABLE II

The Minimal Inhibitory Concentration of Clindamycin and U-57930E vs. Gram-Positive and Gram-Negative Anaerobic Bacteria

| Organism | UC | MIC(μg/ml) Clindamycin | MIC(μg/ml) U-57930E |
|---|---|---|---|
| Bacteroides fragilis | 6513 | 0.06 | 0.12 |
|  | 6428 | 0.06 | 0.25 |

TABLE II-continued

The Minimal Inhibitory Concentration of Clindamycin and U-57930E vs. Gram-Positive and Gram-Negative Anaerobic Bacteria

| Organism | UC | MIC(μg/ml) Clindamycin | U-57930E |
|---|---|---|---|
|  | 6864 | 3.9 | 2.0 |
|  | 6862 | 7.8 | 15.6 |
| Bacteroides thetaiotaomicon | 6512 | 2.0 | 0.5 |
| Bacteroides distasonis | 6518 | 0.12 | ≦0.03 |
| Bacteroides melaninogenicus | 6326 | 0.06 | 0.06 |
| Clostridium perfringens | 247 | 0.06 | 0.12 |
|  | 6509 | 0.06 | 0.12 |
| Clostridium novyi B | 6329 | 0.06 | 0.12 |
| Clostridium tertium | 6508 | 7.8 | 7.8 |
| Clostridium cadaveris | 6510 | ≦0.03 | 0.06 |
| Clostridium sordellii | 6505 | 2.0 | 0.5 |
| Clostridium tentani | 6521 | ≦0.03 | ≦0.03 |
| Clostridium botulinum A | 6506 | 0.25 | ≦0.03 |
| Clostridium bifermentans | 6507 | 0.50 | 0.06 |
| Clostridium difficile | 6834 | 7.8 | 3.9 |
|  | 6857 | 250 | 125 |
|  | 6858 | 3.9 | 3.9 |
|  | 6860 | 500 | 500 |
|  | 6861 | 3.9 | 2.0 |
| Propionibacterium acnes | 6564 | 0.06 | 0.12 |
|  | 6575 | <0.03 | 0.06 |
| Eubacterium limosum | 6515 | 2.0 | 2.0 |
| Eubacterium lentum | 6522 | 0.50 | 1.0 |
| Actinomyces naeslundii | 5920 | 0.25 | 0.25 |
| Fusobacterium nucleatum | 6516 | 0.12 | 0.12 |
|  | 6324 | 0.06 | 0.06 |
| Fusobacterium varium | 6052 | 15.6 | 3.9 |
| Fusobacterium necrophorum | 6568 | 0.06 | 0.06 |
| Peptococcus asaccharolyticus | 6214 | 0.50 | 0.25 |
| Peptococcus magnus | 6258 | 0.06 | 0.06 |
| Peptococcus aerogenes | 6319 | ≦0.03 | 0.06 |
| Peptostreptococcus anaerobius | 6321 | 0.12 | 0.12 |

The procedure for the above test is as follows: Serial two-fold dilutions of drug are prepared in 1.0 ml volumes of Schaedler Broth, and 9.0 ml of molten (47° C.) Wilkens-Chalgrèn Agar Medium, infra, is added to the antibiotic-supplemented broth. After mixing with the antibiotic, the agar is poured into 100 mm×20 mm petri dishes. The dishes are allowed to stand on the bench overnight prior to inoculation.

Cultures are streaked on Wilkens-Chalgren Agar, and grown for 48 hours at 37° C. in a BBL Anaerobe Jar. Growth from the plate is harvested, and a cell suspension is made in Schaedler broth to equal the turbidity of a 0.5 McFarland Standard ($10^8$ cells/ml). The suspension is pipetted into the wells of a Steers replicator, and approx. 1–2 μl is delivered to the surface of the agar plates. After allowing a few minutes for the inoculum to dry, the plates are placed in a BBL Anaerobe Jar (atomsphere of 85% N, 10% H, 5% $CO_2$) and incubated at 37° C. for 72 hours.

The Minimal Inhibitory Concentration (MIC) is read as the least amount of drug that inhibits growth. A very faint film of growth, or <3 is colonies is considered negative.

Wilkins-Chalgren Agar Medium

Dispense the following ingredients and dissolve in 1000 ml distilled water. The pH should be 7.0–7.2.

| | |
|---|---|
| Trypticase | 10 g |
| Gelysate | 10 g |
| Yeast Extract | 5 g |
| Glucose | 1 g |
| NaCl | 5 g |
| L-Arginine-Free Base | 1 g |
| Pyruvic Acid-Sodium Salt | 1 g |
| Agar | 15 g |

Add Heme and +Vitamin $K_1$ solutions to yield final concentrations of 5 μg/ml Hemin and 0.5 g/ml $K_1$. Autoclave at 121° C. for 15 minutes aerobically. Heme Stock—0.5 g Hemin+10 ml 1 N NaOH+990 ml $H_2$.

Autoclave at 121° C. for 12 minutes.

Add 10 ml stock per liter of medium. +Vitamin K Stock-0.05 ml Vit. $K_1$ solution+20 ml 95% ethanol. Filter sterilize.

Add 0.2 ml stock per liter of medium.

The I.P. $LD_{50}$ of U-57,930E in the mouse was found to be 592 mg/kg. This value is the resulting mean of two separate and identical $LD_{50}$ determinations. This value is approximately 2 times the $LD_{50}$ for clindamycin HCl. The $LD_{50}$ value should be interpreted as indicating that the acute I.P. toxicity of U-57,930E is approximately one-half that of clindamycin HCl.

| | In vivo: Mouse Protection Test | | |
|---|---|---|---|
| Organism & Route | Clindamycin | U-57930A | Ratio |
| S. aureus Subcut. | 5.7(4.2–7.8)* | <<5 | — |
| Oral | 12.3(8.8–17.3) | 1–5 | ca.10 |
| S. hemolyticus Subcut. | 2.3(1.6–3.3) | .25 | ca.10 |
| Subcut. | 3.3(2.6–4.2) | .25(0.2–0.33) | 13 |
| Oral | 12.3(10.2–14.8) | 2.9(2.0–4.1) | 4.2 |
| K. pneumoniae | >320 | >320 | — |

*$CD_{50}$'s as mg/kg

The procedure for the above test is as follows:

Mouse-protection Tests: Groups of 10 standard laboratory mice (CF-1 Mice) weighing 18–20 gm were infected with approximately 100 $LD_{50}$'s of standardized bacterial cell suspensions which had been maintained frozen at −170° C. Immediately before use, the suspensions were thawed quickly and properly diluted. Infection was via the intrapertioneal route.

Treatment of the infected groups was begun immediately and continued once per day for 4 days (first 24 hr period=1). Groups of untreated mice served as virulence controls for the culture.

Seven days after the treatment regimen was begun the surviving animals were sacrificed and the median protective dose of the antibiotic calculated on the basis of mortality rates in the treatment groups. The median protective dose and its 95% confidence interval were calculated according to the method of Spearmen & Karber as programmed on a 360 digital computer.

Also isolated from Example I, Part II, is compound V A. This material is obtained as follows:

The filtrate which was saved from Part II was concentrated to dryness under vacuum, the residue converted to its free base and chromatographed over silica gel using CHCl₃:methanol (6:1) as the eluting solvent. In this manner the least polar material mentioned in Part II was obtained. It was converted to its HCl salt and recrystallized from acetone and water. This isomer is tentatively being assigned structure V A.

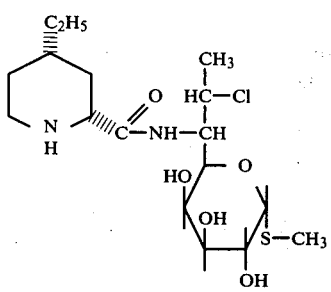

Epimerization of the carbonyl function attached to the piperidine ring of V and V A may be accomplished by methods well known to those skilled in the art. The trans isomers V B and V C produced by these epimerizations may be isolated by conventional procedures such as crystallization or chromatography.

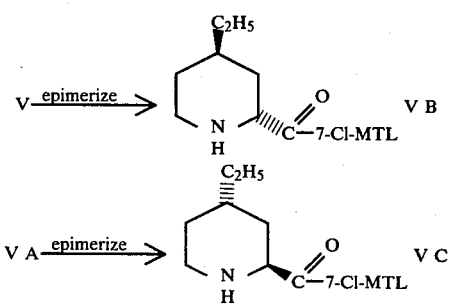

Alternatively, V and V A may be hydrolyzed to give the amino acids V D and V E which may then be epimerized by methods well known to those skilled in the art to V F and V G, respectively. The amino acids V F and V G may be coupled with any of the lincosaminides described earlier.

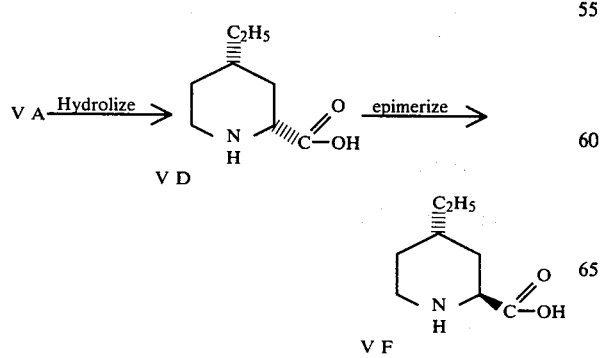

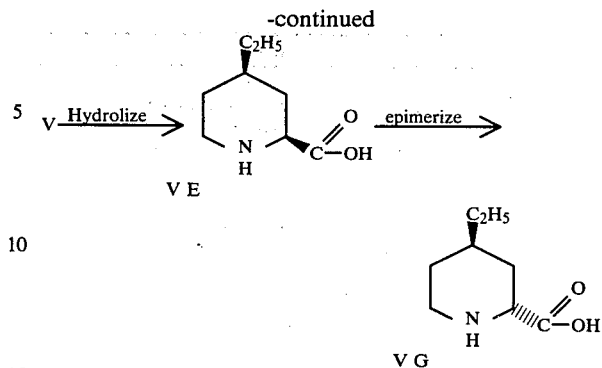

The D-cis isomer (V A) of U-57,930E has an antibacterial spectrum when tested on BHl broth as described previously in Table 1.

| Organism | UC No. | MIC (μg/ml) |
|---|---|---|
| S. aureus | 76 | 250 |
|  | 570 | 1000 |
|  | 746 | 125 |
| S. fecalis | 694 | >1000 |
| S. pyogenes | 152 | 62.5 |
| D. pneumoniae | 41 | 62.5 |
| E. coli | 45 | >1000 |
| K. pneumoniae | 58 | >1000 |
| S. schottmuelleri | 126 | >1000 |
| Ps. aeruginosa | 95 | >1000 |

EXAMPLE 2

Other Analogs of 7-Cl-MTL.

By following the procedures of Example 1, but substituting the amino acid with the following amino acids there are prepared the corresponding novel antibacterially-active analogs as their free bases or acid addition salts. The latter can be prepared by methods well-known to those skilled in the art.

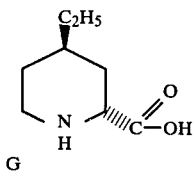

| Amino Acid | Analog |
|---|---|
|  | U-45,863 |
|  | U-46,138 |
|  | U-46,137 |
|  | U-46,337 (Fast isomer on TLC- MeOH:CHCl 95:5. Run on silica gel plates) |
|  | U-46,465 (Slow isomer on TLC) |

-continued

| Amino Acid | Analog |
|---|---|
| [piperidine-N(CH3)-COOH] | U-46,699 (Slow isomer on TLC, prepared from U-46,465) |
| [5-ethyl pyridine-2-COOH] | U-45,656 |
| [4-ethyl pyridine-2-COOH] | U-45,652 |
| [4-ethyl-N-methyl piperidine-2-COOH] | U-46,701 |
| [4-ethyl piperidine-2-COOH, NH] | U-60,481 |
| [piperidine-N(CH2CH2OH)-COOH] | U-44,469 |
| [2-chloro pyridine-3-COOH] | U-45,657 |

EXAMPLE 3

Analogs of MTL

By following the procedures of Example 1, but substituting the amino acid with the following amino acids and substituting MTL (J. Am. Chem. Soc., 89-2448, 1967 W. Schroeder, B. Bannister and H. Hoeksema) for 7-Cl-MTL, there are prepared the corresponding novel antibacterially-active analogs:

| Amino Acid | Analogs |
|---|---|
| [pyridine-2-COOH] | U-46,136 |
| [4-ethyl pyridine-2-COOH] | U-45,653 |
| [3-OH piperidine-2-COOH, NH] | U-60,493 (fast isomer TLC) |

-continued

| Amino Acid | Analogs |
|---|---|
| [piperidine-2-COOH, NH] | U-60,492 (slow isomer TLC) |

EXAMPLE 4

Analogs of ept-MTL

By following the procedures of Example 1, but substituting the amino acid with the following amino acids, and substituting epi-MTL (J. Chem. Soc. Perkin I 1974, p. 306-B, Bannister) for 7-Cl-MTL there are prepared the corresponding novel antibacterially-active analogs:

| Amino acid | Analog |
|---|---|
| [pyridine-2-COOH] | U-46,135 |
| [4-ethyl pyridine-2-COOH] | U-45,659 |
| [piperidine-2-COOH, NH] | Cpd. A |
| [4-ethyl piperidine-2-COOH, NH] | Cpd. B |

EXAMPLE 5

Analogs of epi-7-Cl-MTL

By following the procedures of Example 1, but substituting the amino acid with the following amino acids, and substituting epi-7-Cl-MTL for 7-Cl-MTL, there are prepared the corresponding novel antibacterially-active analogs:

| Amino Acid | Analog |
|---|---|
| [pyridine-2-COOH] | Cpd. C |
| [4-ethyl pyridine-2-COOH] | Cpd. D |
| [piperidine-2-COOH, NH] | Cpd. E |

-continued

| Amino Acid | Analog |
|---|---|
| 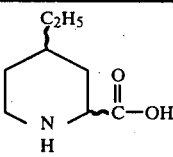 | Cpd. F |

Epi-7-Cl-MTL can be prepared by the procedure used to prepare 7-Cl-MTL with the exception that the starting material is epi-MTL instead of MTL.

Chemical and physical characterization of most of the compounds of Examples 2-5 are as follows:

|  |  | C | H | N | S | Cl | αD | Mp. |
|---|---|---|---|---|---|---|---|---|
| U-45,863 | 1 | 47.80 | 5.62 | 7.44 | 8.51 | 9.41 | CHCl$_3$ | — |
|  | 2 | 47.76 | 5.54 | 7.35 | 8.76 | 9.34 | +286° | 96–100° |
| U-46,138 | 1 | 47.80 | 5.62 | 7.44 | 8.51 | 9.41 | — | — |
|  | 2 | 47.30 | 5.74 | 6.91 | 8.51 | 9.44 |  |  |
| U-46,137 | 1 | 47.80 | 5.62 | 7.44 | 8.51 | 9.41 | EtOH |  |
|  | 2 | 47.58 | 5.74 | 7.56 | 8.53 | 9.49 | +216° | 189–190° |
| U-46,136 | 1 | 50.26 | 6.19 | 7.82 | 8.95 |  | MeOH |  |
|  | 2 | 49.16 | 5.86 | 8.01 | 9.15 |  | +194° | 199–201° |
| U-46,135 | 1 | 50.26 | 6.19 | 7.82 | 8.95 |  | MeOH |  |
|  | 2 | 50.50 | 6.19 | 7.98 | 9.27 |  | +269° | 97–100° |
| U-46,337A | 1 | 42.96 | 6.73 | 6.68 | 7.65 | 16.91 | EtOH |  |
|  | 2 | 42.73 | 6.86 | 6.52 | 7.73 | 16.68 | +206° | 220–30° |
| U-46,465E | 1 | 47.05 | 7.11 | 7.32 | 8.38 | 9.26 | EtOH |  |
|  | 2 | 46.63 | 7.37 | 7.12 | 8.47 | 9.33 | +231° | 180–3° |
| U-46,699E | 1 | 44.34 | 6.98 | 6.47 | 7.40 | 16.36 | H$_2$O |  |
|  | 2 | 44.79 | 7.24 | 6.25 | 7.36 | 16.42 | +172° | 229–234° |
| U-45,656 | 1 | 50.42 | 6.22 | 6.92 | 7.92 | 8.76 | CHCl$_3$ |  |
|  | 2 | 50.85 | 6.39 | 6.72 | 7.54 | 8.93 | +250° | — |
| U-45,652 | 1 | 50.42 | 6.22 | 6.92 | 7.92 | 8.76 | CHCl$_3$ |  |
|  | 2 | 51.03 | 6.40 | 6.65 | 7.56 | 8.02 | +273° | — |
| U-45,653 | 1 | 52.83 | 6.78 | 7.25 | 8.30 | — | MeOH |  |
|  | 2 | 53.83 | 7.08 | 7.39 | 8.14 | — | +203° | — |
| U-45,659 | 1 | 52.83 | 6.78 | 7.25 | 8.30 | — | CHCl$_3$ |  |
|  | 2 | 52.77 | 6.70 | 7.34 | 8.55 | — | +295° | — |
| U-46,701A | 1 | 46.85 | 7.43 | 6.07 | 6.95 | 15.37 |  |  |
|  | 2 | — | — | — | — | — | — | — |
| U-44,469E | 1 | 44.06 | 6.96 | 6.05 | 6.92 | 15.30 |  |  |
|  | 2 | 44.83 | 6.68 | 6.07 | 6.72 | 15.49 | — |  |
| U-45,657 | 1 | 43.80 | 4.90 | 6.81 | 7.80 | 17.24 | MeOH |  |
|  | 2 | 43.52 | 4.93 | 6.82 | 7.82 | 17.41 | +181° | 105–130° |

1 - CALCD.
2 - FOUND

EXAMPLE 6

Fusaric Acid Amide of 7-Chloro-MTL

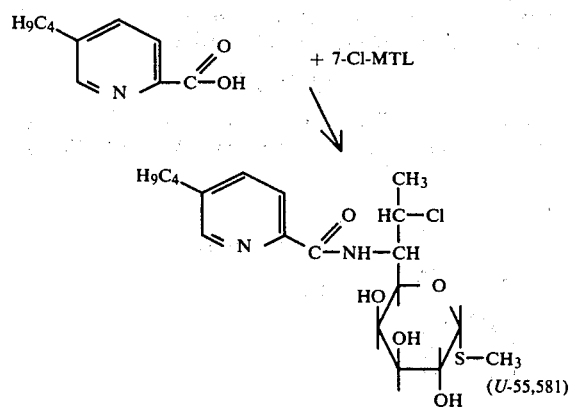

By following the procedure of Example 1, but substituting the amino acid with fusaric acid, there is obtained U-55,581.

Anal. Calcd. for C$_{19}$H$_{29}$ClN$_2$O$_5$S: C, 52.70; H, 6.75; N, 6.47; S, 7.41; Cl, 8.19. Found: C, 51.15; H, 6.65; N, 6.36; S, 7.21; Cl, 7.94.

EXAMPLE 7

4-Cis-n-Butyl-L-Pipecolic Acid Amide of 7-Cl-MTL or U-50,970E

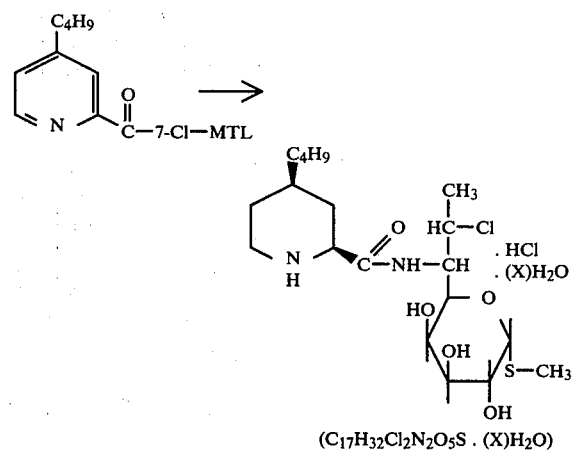

A mixture of 4.0 g (0.0093 mole) of starting material, 40 ml of water, 40 ml of methanol, 2 ml of 37% HCl, and 8.0 g. PtO$_2$ catalyst were reduced on a Parr hydrogenator at 50 psi for 18 hours. The reaction was filtered to remove the catalyst and the filtrate concentrated under vacuum to give an amber oil. The oil was dissolved in 20 ml. of a 2:1 solution of CHCl$_3$ and methanol and enough triethylamine added to neutralize the HCl present. This solution was then chromatographed over silica gel using a solvent system composed of CHCl$_3$:methanol (2:1). Two main product fractions are obtained. The fractions containing the faster moving material were pooled and evaporated under vacuum to give a white solid, fraction A. The fractions containing the slower moving material were pooled and evaporated under vacuum to give a white solid, fraction B. Fraction B was dissolved in a small amount of H$_2$O and enough 37% HCl added to make the pH 2. Crystallization occurred. The solid was collected and recrystallized from H$_2$O to give white crystals of the desired product, U-60,970E, m.p. 224°–226° in a yield of 25-35%.

Anal. Calcd. for C$_{17}$H$_{32}$Cl$_2$N$_2$O$_5$S: C, 47.99; H, 7.63; N, 5.89; S, 6.75; Cl, 14.92. Found: C, 47.97; H, 7.42; N, 6.23; S, 6.90; Cl, 14.87. $\alpha_D^{MeOH}+178°$ (C, 1.0).

CMR analysis supports the proposed structure.

The Minimal Inhibitory Concentration (MIC) in μg/ml of U-60,970E against various bacteria is as follows:

| Organism | UC# | MIC |
|---|---|---|
| S. aureus | 76 | 0.125 |
|  | 570 | 0.25 |
|  | 746 | 0.062 |
| S. faecalis | 694 | 0.25 |
| S. pyogenes | 152 | 0.008 |
| D. pneumoniae | 41 | 0.016 |
| E. coli | 45 | 31.2 |
| K. pneumoniae | 58 | 7.8 |

| Organism | UC# | MIC |
|---|---|---|
| S. schottmuelleri | 126 | 31.2 |
| Ps. aeruginosa | 95 | >125 |

The test procedure is as disclosed in Example 1.

U-60,970E was also tested in vivo in standard laboratory mice which were experimentally infected with bacteria. The test was conducted in comparison with U-57,930E. The following results show that U-60,970E is significantly more active in vivo against *D. pneumoniae* I and III than U-57,930E. Against *S. aureus* and *S. hemolyticus* U-60,970E demonstrated essentially the same activity as U-57,930E.

| | | Median Portective Dose (CD$_{50}$ in mg/kg) | | | |
|---|---|---|---|---|---|
| | | U-57930E . Hcl | | U-60970E . Hcl | |
| Organism | Strain | Subcutaneous | Oral | Subcutaneous | Oral |
| S. hemolyticus | C203 | 0.38 (0.28–0.51) | 3.79 (2.74–5.29) | 0.35 | 2.18 (1.5–3.16) |
| S. aureus | UC 76 | 1.07 (0.72–1.59) | 8.12 (5.78–11.41) | 1.32 (1.05–1.66) | 8.12 (6.75–9.77) |
| D. pneumoniae I | Felton I | 1.54 (1.12–2.11) | 15.39 (10.57–22.4) | 0.67 (0.52–0.86) | 4.42 (3.15–6.21) |
| D. pneumoniae III | MPI III | 2.68 (1.88–3.81) | 14.36 (9.68–21.31) | 0.44 (0.36–0.54) | 3.13 (2.26–4.32) |
| | | 2.5 (1.69–3.69) | 16.49 (10.51–25.88) | 0.29 (0.21–0.41) | 4.12 (2.93–5.81) |

EXAMPLE 8

4-Cis-n-Butyl-D-Pipecolic Acid Amide of 7-Cl-MTL or U-61,734E

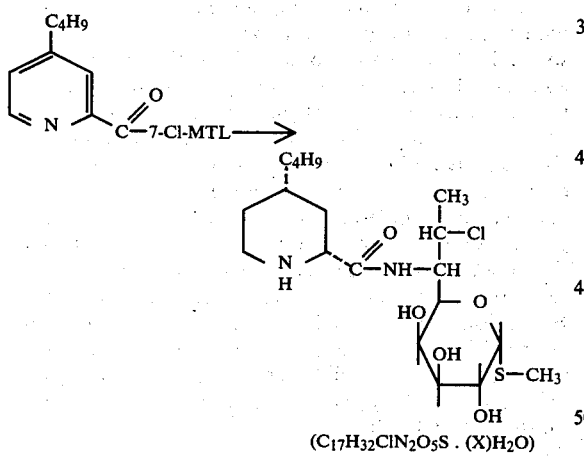

($C_{17}H_{32}ClN_2O_5S \cdot (X)H_2O$)

Fraction A from the preceding experiment was converted to its HCl salt in the same manner as described for fraction B. A 25–35% yield of product was obtained whose CMR spectrum was essentially identical to that obtained from fraction B.

EXAMPLE 9

Preparation of a Compound in Which the Amino-acid Portion Contains a Heteroatom In a 5-Membered Ring

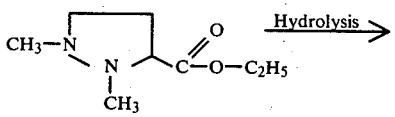

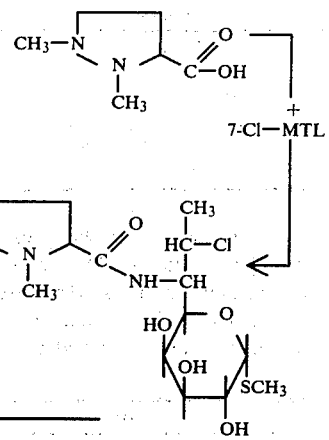

The aminoacid ester (see C.A. 69-67282M) may be hydrolyzed to the free acid by methods well known to those skilled in the art (acid or basic hydrolysis may be used). It may be obtained in the form of the HCl salt or the zwitterion. The coupling of the aminoacid HCl with 7-Cl-MTL is accomplished in the same manner as described in Example 1, except that 67.7 g. (0.357 moles) of the aminoacid is used. After workup, as described in Example 1, the crude product may be purified via chromatography over silica gel and the product fractions combined and converted to the HCl salt.

EXAMPLE 10

Preparation of a Compound in Which the Aminoacid Portion Contains a Heteroatom in a 6-Membered Ring

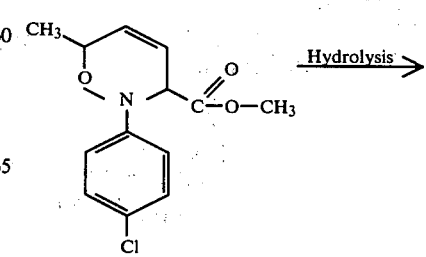

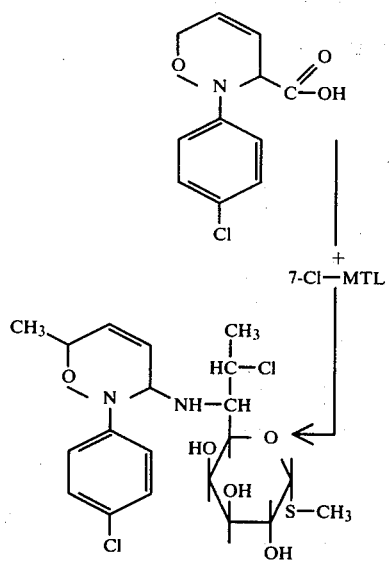

The aminoacid ester (see C.A. 68-59465N) may be hydrolyzed to the free acid by methods well known to those skilled in the art (acid or basic hydrolysis may be used). It may be obtained in the form of the HCl salt or the zwitterion. The coupling of the aminoacid-HCl with 7-Cl-MTL is accomplished in the same manner as described in Example 1 except that 103.6 g. (0.357 moles) of the aminoacid is used. After workup, as described in Example 1, the crude product may be purified via chromatography over silica gel and the product fractions combined and converted to the HCl salt.

EXAMPLE 11

2 Phosphate Analogs

The 2-phosphate analog of the compounds prepared in Examples 1-10 can be prepared by procedures well-known to those skilled in the art. By obvious appropriate modification, the procedure disclosed in U.S. Pat. No. 3,487,068 may be used. Basically, any procedure would first involve the protection of vulnerable groups by methods well-known to those skilled in the art which would then be removed upon completion of the phosphorylation.

EXAMPLE 12

2 Palmitate Analogs

The 2-palmitate analog of the compounds prepared in Examples 1-10 can be prepared by procedures well-known to those skilled in the art. By obvious appropriate modification, the procedure disclosed in U.S. Pat. No. 3,580,904 may be used. Basically, any procedure would first involve the protection of vulnerable groups by methods well-known to those skilled in the art which would then be removed upon completion of the acylation with palmitoyl chloride.

The Minimal Inhibitory Concentration (MIC's) of a representative number of the compounds prepared in Examples 2-8 follows. The test procedure is as given supra.

| | MIC in mcg/ml | | | | | | |
|---|---|---|---|---|---|---|---|
| | U-Number and Structure | | | | | | |
| | 45,656 | 45,652 | 45,653 | 45,659 | 46,701 | 44,469 | 45,657 |
| S. aureus UC 76 | 62.5 | 1000 | >1000 | >1000 | 62.5 | 250 | 125 |
| S. aureus UC 570 | 62.5 | >1000 | >1000 | >1000 | 125 | 250 | 250 |
| S. aureus UC 746 | 62.5 | 1000 | >1000 | 1000 | 625 | >1000 | 250 |
| S. hemolyticus UC 152 | 3.9 | 500 | >1000 | 500 | — | 31.3 | 7.8 |
| St. faecalis UC 694 | 1000 | >1000 | >1000 | >1000 | 500 | 1000 | >1000 |
| S. lutea UC 130 | | | | | 1000 | | |
| E. coli UC 45 | >1000 | >1000 | >1000 | >1000 | >1000 | >1000 | >1000 |
| P. vulgaris UC 93 | >1000 | >1000 | >1000 | >1000 | >1000 | >1000 | >1000 |
| K. pneumoniae UC 58 | 1000 | 500 | >1000 | 1000 | >1000 | >1000 | >1000 |
| S. schottmuelleri UC 126 | 1000 | >1000 | >1000 | >1000 | >1000 | >1000 | >1000 |
| Ps. aeruginosa UC 95 | >1000 | >1000 | >1000 | 1000 | >1000 | >1000 | >1000 |
| D. pneumoniae UC 41 | — | 500 | >1000 | 500 | — | 31.3 | — |

$X = \overset{O}{\underset{\|}{C}}-7\text{-Cl}-\text{MTL}$ $Y = \overset{O}{\underset{\|}{C}}-\text{MTL}$ $Z = \overset{O}{\underset{\|}{C}}-\text{epi-MTL}$ $R = C_2H_5-$

| | MIC in mcg/ml U-Number and Structure | | | | | | | |
|---|---|---|---|---|---|---|---|---|
| | 45,863 | 46,138 | 46,137 | 46,136 | 46,135 | 46,337 | 46,465 | 46,699 |
| | ⟨N⟩-X | ⟨N⟩-X | X-⟨N⟩ | ⟨N⟩-Y | ⟨N⟩-Z | ⟨NH⟩-X | ⟨NH⟩-X | ⟨N-CH₃⟩-X |
| S. aureus UC 76 | 62.5 | | >1000 | >1000 | >1000 | 1000 | 3.9 | 3.9 |
| S. aureus UC 570 | | | >1000 | >1000 | >1000 | 1000 | 31.2 | 7.8 |
| S. aureus UC 746 | | | >1000 | >1000 | >1000 | 1000 | 3.9 | 7.8 |
| S. hemolyticus UC 152 | 2.0 | Qual. | 1000 | 1000 | 1000 | 250 | <1.0 | 3.9 |
| St. faecalis UC 694 | >1000 | Assay Inactive vs. S. lutea | >1000 | >1000 | >1000 | >1000 | 3.9 | 15.6 |
| E. coli UC 45 | >1000 | | 1000 | >1000 | >1000 | >1000 | >1000 | 1000 |
| P. vulgaris UC 93 | >1000 | | >1000 | >1000 | >1000 | >1000 | 1000 | 1000 |
| K. pneumoniae UC 58 | >1000 | | 1000 | >1000 | >1000 | >1000 | 500 | 250 |
| S. schottmuelleri UC 126 | >1000 | | 1000 | >1000 | >1000 | >1000 | 1000 | >1000 |
| Ps. aeruginosa UC 95 | >1000 | | 1000 | >1000 | >1000 | >1000 | >1000 | >1000 |
| D. pneumoniae UC 41 | 62.5 | | 500 | >1000 | >1000 | 250 Fast isomer on TLC | <1.0 Slow isomer on TLC | <1.0 N-methyl of slow isomer |

X = C(=O)—7-Cl—MTL
Y = C(=O)—MTL
Z = C(=O)—epi-MTL

| | MIC in mcg/ml U-Number and Structure | | |
|---|---|---|---|
| | U-60,493 | U-60,492 | U-60,481 |
| | ⟨NH⟩-Y | ⟨NH⟩-Y | R-⟨NH⟩-X |
| S. aureus UC 76 | 1000 | 1000 | 2.0 |
| S. aureus UC 570 | 1000 | >1000 | 3.9 |
| S. aureus UC 746 | 250 | 250 | 2.0 |
| S. hemolyticus UC 152 | 7.8 | 15.6 | >1.0 |
| St. faecalis UC 694 | 1000 | >1000 | 31.2 |
| S. lutea UC 13C | | | |
| E. coli UC 45 | >1000 | >1000 | 500 |
| P. vulgaris UC 93 | >1000 | >1000 | 1000 |
| K. pneumoniae UC 58 | >1000 | >1000 | 250 |
| S. Schottmuelieri UC 126 | >1000 | >1000 | 1000 |
| Ps. aeruginosa UC 95 | >1000 | >1000 | >1000 |
| D. pneumoniae UC 41 | 15.6 Fast isomer on TLC | 31.2 Slow isomer on TLC | — IR & NMR OK |

X = C(=O)—7-Cl—MTL
Y = C(=O)—MTL
R = C₂H₅

Since the compounds of the subject invention are active against various Gram-positive and Gram-negative microbes, they can be used in various environments to inhibit such microbes. For example, they can be used as disinfectants to inhibit S. aureus on washed and stacked food utensils contaminated with this bacterium. They also can be used as disinfectants on various dental and medical equipment contaminated with S. aureus. Further, the compounds of the invention can be used as bacteriostatic rinses for laundered cloths, and for impregnating papers and fabrics; and, they are also useful for suppressing the growth of sensitive organisms in plate assays and other microbiological media.

The compounds of the subject invention exist in the protonated or non-protonated forms according to the pH of the environment. When the protonated form is intended, the compounds exist as pharmaceutically-acceptable acid-addition salts, and when the non-protonated form is intended, the compounds exist as the free base. The free bases can be converted to stable acid-addition salts by neutralizing the free base with the appropriate acid, about pH 7.0, and advantageously to about pH 2 to pH 6. Suitable acids for this purpose include hydrochloric, sulfuric, phosphoric, thiocyanic, fluosilicic, hexafluoroarsenic, hexafluorophosphoric, acetic, succinic, citric, lactic, maleic, fumaric, pamoic, cholic, plamitic, mucic, camphoric, glutaric, glycolic, phthalic, tartaric, lauric, stearic, salicyclic, 3-phenylsalicyclic, 5-phenylsalicyclic, 3-methylglutaric, orthosulfobenzoic, cyclohexanesulfamic, cyclopentanepropionic, 1,2-cyclohexanedicarboxylic, 4-cyclohexanecarboxylic, octadecenylsuccinic, octenylsuccinic, methanesulfonic, helianthic, Reinecke's, dimethyldithiocarbamic, hexadecylsulfamic, octadecylsulfamic, sorbic, monochloroacetic, undecylenic, 4'-hydroxyazobenzene-4-sulfonic, octadecysulfuric, picric, benzoic, cinnamic, and like acids.

The acid-addition salts can be used for the same purposes as the free base or they can be employed to upgrade the same. For example, the free base can be converted to a water-insoluble salt, such as the picrate, which can be subjected to purification procedures, for example, solvent extractions and washings, chromatography, fractional liquid-liquid extractions, and crystallization, and then used to regenerate the free base form by treatment with alkali or to make a different salt by metathesis. Or the free base can be converted to a water-soluble salt, such as the hydrochloride or sulfate, and the aqueous solution of the salt extracted with various water-immiscible solvents before regenerating the free base form by treatment of the thus-extracted acid solution, or converted to another salt by metathesis.

In addition to the antibacterial uses, disclosed above, the free bases can be used as buffers or as antacids. The thiocyanic acid addition salt when condensed with formaldehyde forms resinous materials useful as pickling inhibitors according to U.S. Pat. Nos. 2,425,320 and 2,606,155. The free bases also make good vehicles for toxic acids. For example, the fluosilicic acid addition salts are useful as mothproofing agents according to U.S. Pat. Nos. 1,915,334 and 2,075,359 and the hexafluoroarsenic acid and hexafluorophosphoric acid addition salts are useful as parasiticides according to U.S. Pat. Nos. 3,122,536 and 3,122,552.

The compounds of the subject invention are useful as antibacterial agents in suitable compositions. These compositions are preferably presented for administration to humans and animals in unit dosage forms, such as tablets, capsules, pills, powders, granules, sterile parenteral solutions or suspensions, and oral solutions or suspensions, and oil-water emulsions containing suitable quantities of the active compound in the form of the free base, or its pharmacologically acceptable salts.

For oral administration, either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form according the advantage of prolonged or delayed action or predetermined successive action of the enclosed medication. For example, the tablet can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixture of polymeric acids with such materials as shellac, cetyl alcohol, cellulose acetate phthalate, styrene malenic acid copolymer and the like. Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the compound of the formulation with an inert pharmaceutical diluent and filling and mixture into a hard gelatin capsule of appropriate size. In another embodiment, capsules are prepared by filling hard gelatin capsules with polymeric acid coated beads containing the active compound. Soft gelatin capsules are prepared by machine encapsulation of a slurry of the active compound with an acceptable vegetable oil, light liquid petrolatum or other inert oil.

Fluid unit dosage forms for oral administration such as syrups, elixirs, and suspensions can be prepared. The water-soluble forms of the active compound can be dissolved in an aqueous vehicle together with sugar, aromatic flavoring agents and preservatives to form a syrup. An elixir is prepared by using a hydro-alcoholic (ethanol) vehicle with suitable sweeteners such as sucrose together with an aromatic flavoring agent. Suspensions can be prepared of the insoluble forms with a syrup vehicle with the aid of a suspending agent such as acacia, tragacanth, methylcellulose and the like.

Topical ointments can be prepared by dispersing the active compound in a suitable ointment base such as petrolatum, lanolin, polyethylene glycols, mixtures thereof, and the like. Advantageously, the compound is finely divided by means of a colloid mill utilizing light liquid petrolatum as a levigating agent prior to dispersing in the ointment base. Topical creams and lotions are prepared by dispersing the compound in the oil phase prior to the emulsification of the oil phase in water.

For parenteral administration, fluid unit dosage forms are prepared utilizing the active compound and a sterile vehicle, water being preferred. The active compound, depending on the form and concentration used, can be either suspended or dissolved in the vehicle. In preparing solutions, a water-soluble form of the active compound can be dissolved in water for injection and filter sterilized before filling into a suitable vial or ampul and sealing. Advantageously adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the powder prior to use. Parenteral suspensions are prepared is substantially the same manner except that the active compound is suspended in the vehicle instead of being dissolved and sterilization cannot be accomplished by filtration. The active compound can be sterilized by exposure to ethylene oxide before suspending the sterile vehicle. Advantageously, a surfactant or wetting agent is included in the composition to facilitate uniform distribution of the active compound.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, pills, troches, suppositories, powder packets, granules, wafers, cachets, teaspoonfuls, tablespoonfuls, dropperfuls, ampuls, vials, segregated multiples of any of the foregoing, and other forms as herein described.

In addition to the administration of the active compound as the principal active ingredient of compositions for the treatment of the conditions described herein, the said compound can be included with other types of compounds to obtain advantageous combinations of properties. Such combinations include the active compound with antibiotics such as spectinomycin, chloramphenicol, novobiocin, dihydronovobiocin, tetracyclines (e.g., tetracycline, oxytetracycline and chlortetracycline), penicillins, erythromycin, kanamycin, streptomycin, neomycin, polymyxin, bacitracin, nystatin, filipin, fumagillin and endomycin to broaden the bacterial spectrum of the composition and for synergistic action against particular bacteria; steroids having anti-inflammatory activity such as hydrocortisone, prednisolone, 6α-methylprednisolone, 6α-fluoroprednisolone and the like; analgesics such as aspirin, sodium salicylate (acetylsalicylic acid)anydride, N-acetyl p-aminophenyl and salicylamide; antihistamines, such as chlorpheniramine maleate, diphenylhydramine, promethazine, pyrathiazine, and the like; sulfas, such as sulfadiazine, sulfamethazine, sulfamerazine sulfacetamide, sulfadimethyloxazole, sulfamethizole, and the like; antifungals, such as undecylenic acid, sodium propionate, salicylanilide, sodium caprylate, and hexetidine; and the vitamins.

The dosage of the active compound for treatment depends on route of administration; the age, weight, and condition of the patient; and the particular disease to be treated. A dosage schedule of from about 15 to 500 mg., 1 to 4 times daily (every six hours), embraces the effective range for the treatment of most conditions for which the compositions are effective. For children, the dosage is calculated on the basis of 15 to 30 mg./kg./day to be administered every six hours.

The active compound is compounded with a suitable pharmaceutical carrier in unit dosage form for convenient and effective administration. In the preferred embodiments of this invention, the dosage units contain the compound in: 15, 30, 50, 125, 250 and 500 mg. amounts for systemic treatment; in 0.25, 0.5, 1, 2 and 5% amounts for topical or localized treatment; and 5 to 65% w/v for parenteral treatment. The dosage of compositions containing the active compound and one or more other active ingredients is to be determined with reference to the usual dosage of each such ingredient.

The following examples are illustrative of the best mode contemplated by the inventor for carrying out his invention and are not to be construed as limiting.

The examples use U-57,930E or U-60,970E as the active compound, but it should be understood that this is only exemplary of the other active compounds of the subject invention. As distinguished from the previous examples, the following are Composition Examples.

COMPOSITION EXAMPLE 1

Capsules

One thousand two-piece hard gelatin capsules for oral use, each containing 250 mg. of U-57,930E or U-60,970E are prepared from the following types and amounts of materials:

|  | Gm. |
| --- | --- |
| U-57,930E or U-60,970E | 250 |
| Corn starch | 100 |
| Talc | 75 |
| Magnesium stearate | 25 |

The materials are thoroughly mixed and then encapsulated in the usual manner.

The foregoing capsules are useful for the systemic treatment of infection in adult humans by the oral administration of 1 capsule every 4 hours.

Using the procedure above, capsules are similarly prepared containing U-57,930E or U-60,970E in 15, 30, 50, 125 and 500 mg. amounts by substituting 15, 30, 50, 125, and 500 mg of U-57,930E or U-60,970E for the 250 gm used above.

COMPOSITION EXAMPLE 2

Capsules

One thousand two-piece hard gelatin capsules for oral use, each containing 200 mg. of U-57,930E or U-60,970E and 250 mg. of tetracycline hydrochloride, are prepared from the following types and amounts of ingredients:

|  | Gm. |
| --- | --- |
| U-57,930E or U-60,970E | 200 |
| Tetracycline hydrochloride | 250 |
| Talc | 75 |
| Magnesium stearate | 25 |

The ingredients are thoroughly mixed and then encapsulated in the usual manner.

The foregoing capsules are useful for the systemic treatment of infection in adult humans by the oral administration of 1 capsule every 6 hours.

Using the procedure above, capsules are similarly prepared containing U-57,930E or U-60,970E and each of the following antibiotics in place of tetracycline by substituting 250 gm. of such other antibiotic for tetracycline: chloramphenicol, oxytetracycline, chlortetracycline, fumagillin, erythromycin, streptomycin, dihydronovobiocin and novobiocin. When a penicillin, such as potassium penicillin G, is to be used in place of tetracycline, 250,000 units per capsule is employed.

Such combination products are useful for the systemic treatment of mixed infections in adult humans by the oral administration of 1 capsule every 6 hours.

COMPOSITION EXAMPLE 3

Tablets

One thousand tablets for oral use, each containing 500 mg. of U-57,930E or U-60,970E are prepared from the following types and amounts of materials:

|  | GM. |
|---|---|
| U-57,930E or U-60,970E | 500 |
| Lactose | 125 |
| Corn starch | 65 |
| Magnesium stearate | 25 |
| Light liquid petrolatum | 3 |

The ingredients are thoroughly mixed and slugged. The slugs are broken down by forcing through a number sixteen screen. The resulting granules are then compressed into tablets, each tablet containing 500 mg. of U-57,930E or U-60,970E.

The foregoing tablets are useful for systemic treatment of infections in adult humans by oral administration of 1 tablet every 4 hours.

Using the above procedure, except for reducing the amount of U-57,930E to U-60,970E to 250 gm., tablets containing 250 mg. of U-57,930E or U-60,970E are prepared.

COMPOSITION EXAMPLE 4

Tablets

One thousand oral tablets, each containing 250 mg. of U-57,930E or U-60,970E, and a total of 250 mg. (83.3 mg. each) of sulfadiazine, sulfamerazine, and sulfamethazine, are prepared from the following types and amounts of materials:

|  | Gm. |
|---|---|
| U-57,930E or U-60,970E | 250 |
| Sulfadiazine | 83.3 |
| Sulfamerazine | 83.3 |
| Sulfamethazine | 83.3 |
| Lactose | 50 |
| Corn starch | 50 |
| Calcium stearate | 25 |
| Light liquid petrolatum | 5 |

The ingredients are thoroughly mixed and slugged. The slubs are broken down by forcing through a number sixteen screen. The resulting granules are then compressed into tablets, each containing 250 mg. of U-57,930E or U-60,970E and a total of 250 mg. (83.3 mg. each) of sulfadiazine, sulfamerazine, and sulfamethazine.

The foregoing tablets are useful for systemic treatment of infections by the oral administration of 4 tablets first and then 1 every six hours.

For the treatment of urinary infections, the triple sulfas in the above formulation is advantageously replaced by 250 gm. of sulfamethylthiadiazole or 250 gm. of sulfacetamide.

COMPOSITION EXAMPLE 5

Oral Syrup

One thousand cc. of an aqueous suspension for oral use, containing in each 5 cc. dose, one-half gram of total sulfas and 250 mg. of U-57,930E or U-60,970E is prepared from the following types and amounts of ingredients:

|  | Gm. |
|---|---|
| U-57,930E or U-60,970E | 50 |
| Sulfadiazine | 33.3 |
| Sulfamerazine | 33.3 |
| Sulfamethazine | 33.3 |
| Citric acid | 2 |
| Benzoic acid | 1 |
| Sucrose | 700 |
| Tragacanth | 5 |
| Lemon oil 2 cc. | |
| Deionized water, q.s. 1,000 cc. | |

The citric acid, benzoic acid, sucrose, tragcanth, and lemon oil are dispersed in sufficient water to make 850 cc. of solution. The U-57,930E or U-60,970E and finely powdered sulfas are stirred into the syrup until uniformly distributed. Sufficient water is added to make 1,000 cc.

The composition so prepared is useful in the systemic treatment of pneumonia in adult humans at a dose of 1 teaspoonful 4 times a day.

COMPOSITION EXAMPLE 6

Parenteral Solution

A sterile aqueous solution for intramuscular use, containing in 1 cc. 200 mg. of U-57,930E or U-60,970E is prepared from the following types and amounts of materials:

|  | Gm. |
|---|---|
| U-57,930E or U-60,970E | 200 |
| Lidocaine hydrochloride | 4 |
| Methylparaben | 2.5 |
| Water for injection, q.s. 1,000 cc. | |

The ingredients are dissolved in water and the solution sterilized by filtration. The sterile solution is filled into vials and the vials sealed.

COMPOSITION EXAMPLE 7

Parenteral Preparation

A sterile aqueous solution for intramuscular use, containing in 1 cc. 200 mg. of U-57,930E and U-60,970E and 400 mg. of spectinomycin sulfate, is prepared from the following types and amounts of ingredients:

|  | Gm. |
|---|---|
| U-57,930E or U-60,970E | 200 |
| Spectinomycin sulfate | 400 |
| Lactose | 50 |
| Water for injection, q.s. 1,000 cc. | |

The U-57,930E or U-60,970E, spectinomycin sulfate and lactose are dissolved in the water and the solution sterilized by filtration. The sterile solution, in the amount of 2 cc., is aseptically filled into sterile vials and frozen. The water is removed under high vacuum and the vials containing the lyophilized powder are sealed. Just prior to use, sufficient sterile water for injection to make 2 cc. of solution is added to the vial.

COMPOSITION EXAMPLE 8

Topical Ointment

One thousand gm. of 0.25% ointment is prepared from the following types and amounts of ingredients:

|  | Gm. |
| --- | --- |
| U-57,930E or U-60,970E | 2.5 |
| Zinc oxide | 50 |
| Calamine | 50 |
| Liquid petrolatum (heavy) | 250 |
| Wool fat | 200 |
| White petrolatum, q.s. 1,000 gm |  |

The white petrolatum and wool fat are melted and 100 gm. of liquid petrolatum added thereto. The U-57,930E or U-60,970E, zinc oxide and calamine are added to the remaining liquid petrolatum and the mixture milled until the powders are finely divided and uniformly dispersed. The powder mixture is stirred into the white petrolatum mixture and stirring continued until the ointment congeals.

The foregoing ointment is usefully applied topically to the skin of mammals for the treatment of infection.

The foregoing composition can be prepared by omitting the zinc oxide and calamine.

Following the procedure above, ointments are similarly prepared containing U-57,930E or U-60,970E in 0.5, 1, 2, and 5% amounts by substituting 5, 10, 20 and 50 gm. of U-57,930E or U-60,970E for the 2.5 gm. used above.

COMPOSITION EXAMPLE 9

Cream

One thousand gm. of a vaginal cream are prepared from the following types and amounts of ingredients:

|  | Gm. |
| --- | --- |
| U-57,930E or U-60,970E | 50 |
| Tegacid Regular[1] | 150 |
| Spermaceti | 100 |
| Propylene glycol | 50 |
| Polysorbate 80. | 5 |
| Methylparaben | 1 |
| Deionized water, q.s. 1,000 gm. |  |

[1]Self-emulsifying glyceryl monostearate from Goldschmidt Chemical Corporation, New York, N.Y.

The Tegacid and spermaceti are melted together at a temperature of 70°-80° C. The methylparaben is dissolved in about 500 gm. of water and the propylene glycol, Polysorbate 80, and U-57,930E or U-60,970E are added in turn, maintaining a temperature of 75°-80° C. The methylparaben mixture is added slowly to the Tegacid and spermaceti melt, with constant stirring. The addition is continued for at least 30 minutes with continued stirring until the temperature has dropped to 40°-45° C. The pH of the final cream is adjusted to 3.5 by incorporating 2.5 gm. of citric acid and 0.2 g. of dibasic sodium phosphate dissolved in about 50 gm. of water. Finally, sufficient water is added to bring the final weight to 1,000 gm. and the preparation stirred to maintain homogeneity until cooled and congealed.

The foregoing composition is useful for the treatment of vaginal infections in humans.

COMPOSITION EXAMPLE 10

Ointment, Ophthalmic

One thousand gm. of an ophthalmic ointment containing 0.5% U-57,930E or U-60,970E are prepared from the following types and amounts of ingredients:

|  | Gm. |
| --- | --- |
| U-57,930E or U-60,970E | 5 |
| Bacitracin | 12.2 |
| Polymyxin 3 sulfate (10,000 units/mg.) | 1 |
| Light liquid petrolatum | 250 |
| Wool fat | 200 |
| White petrolatum, q.s. 1,000 gm. |  |

The solid ingredients are finely divided by means of an air micronizer and added to the light liquid petrolatum. The mixture is passed through a colloid mill to uniformly distribute the micronized particles. The wool fat and white petrolatum are melted together, strained, and the temperature adjusted to 45°-50° C. The liquid petrolatum slurry is added and the ointment stirred until congealed. Suitably the ointment is packaged in one dram ophthalmic tubes.

The foregoing ointment is usefully applied to the eye for treatment of localized infection in humans and other animals.

Advantageously the foregoing composition can contain 5 gm. (0.5%) of methylprednisolone for the treatment of inflammation, and, alternatively, the bacitracin and polymyxin B sulfate can be omitted.

COMPOSITION EXAMPLE 11

Eye-Ear Drops

One thousand cc. of a sterile aqueous solution for eye or ear use containing 10 mg. of U-57,930E or U-60,970E and 5 mg. of methylprednisolone in each cc. is prepared from the following types and amounts of ingredients:

|  | Gm. |
| --- | --- |
| U-57,930E or U-60,970E | 10 |
| Methylprednisolone phosphate sodium | 5 |
| Sodium citrate | 4.5 |
| Sodium bisulfite | 1 |
| Polyethylene glycol 4000 | 120 |
| Nyristyl-γ-picolinium chloride | 0.2 |
| POlyvinylpyrrolidone | 1 |
| Deionized water, q.s. ad 1000 cc. |  |

The ingredients are dissolved in the water and the resulting solution is sterilized by filtration. The solution is aseptically filled into sterile dropper containers.

The composition so prepared is useful in the topical treatment of inflammation and infection of the eye and ear as well as other sensitive tissues of the animal body.

COMPOSITION EXAMPLE 12

Troches

Ten thousand troches are prepared from the following types and amounts of ingredients:

|  | Gm. |
| --- | --- |
| U-57,930E or U-60,970E | 100 |
| Neomycin sulfate | 50 |

-continued

| | Gm. |
|---|---|
| Polymyxin B sulfate (10,000 units/mg.) | 1 |
| Ethyl aminobenzoate | 50 |
| Calcium stearate | 150 |
| Powdered sucrose, q.s. 5,000 gm. | |

The powdered materials are mixed thoroughly and then compressed into half gram troches following the usual techniques for the preparation of compressed tablets.

The troches are held in the mouth and allowed to dissolve slowly to provide treatment for the mouth and throat of humans.

COMPOSITION EXAMPLE 13

Suppository, Rectal

One thousand suppositories, each weighing 2.5 gm. and containing 100 mg. of U-57,930E or U-60,970E are prepared from the following types and amounts of ingredients:

| | Gm. |
|---|---|
| U-57,930E or U-60,970E | 100 |
| Polymyxin B sulfate (10,000 units/mg.) | 1.25 |
| Methylprednisolone | 75 |
| Zinc oxide | 62.5 |
| Propylene glycol | 162.5 |
| Polyethylene glycol 4,000 q.s. | 2,500 gm. |

The U-57,930E or U-60,970E, polymyxin B sulfate, methylprednisolone, ethyl aminobenzoate, and zinc oxide are added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C.

The composition is allowed to cool and solidify and then removed from the mold and each suppository foil wrapped.

The foregoing suppositories are inserted rectally for local treatment of inflammation and infection.

Alternatively, the foregoing composition can be prepared omitting the steroid.

COMPOSITION EXAMPLE 14

Mastitis Ointment

One thousand gm. of an ointment for the treatment of mastitis in dairy cattle is prepared from the following types and amounts of ingredients:

| | Gm. |
|---|---|
| U-57,930E or U-60,970E | 25 |
| Methylprednisolone acetate | 0.5 |
| Light liquid petrolatum | 300 |
| Chlorobutanol, anhydrous | 5 |
| Polysorbate 80 | 5 |
| 2% Aluminum monostearate-peanut oil gel | 400 |
| White petrolatum, q.s. 1000 gm. | |

The U-57,930E or U-60,970E and methylprednisolone acetate are milled with the light liquid petrolatum until finely divided and uniformly dispersed. The chlorobutanol, polysorbate 80, peanut oil gel and white petrolatum are heated to 120° F. to form a melt and the liquid petrolatum dispersion stirred in. With continued stirring, the dispersion is allowed to cool (and congeal) to room temperature and is filled into disposable mastitis syringes in 10 gm. doses.

COMPOSITION EXAMPLE 15

Animal Feed

One thousand gm. of a feed mix is prepared from the following types and amounts of ingredients:

| | Gm. |
|---|---|
| U-57,930E or U-60,970E | 10 |
| Soybean meal | 400 |
| Fish meal | 400 |
| Wheat germ oil | 50 |
| Sorghum molasses | 140 |

The ingredients are mixed together and pressed into pellets. The composition can be fed to laboratory animals, i.e., rats, mice, guinea pigs, and hamsters for prophylaxis during shipping.

For other animals such as poultry, e.g., chickens, ducks, turkeys, and geese, the composition can be added to the animal's regular feed in an amount calculated to give the desired dose of U-57,930E or U-60,970E.

COMPOSITION EXAMPLE 16

Following the procedure of each of the preceding Composition Examples 1–15, inclusive, each antibacterially-active compound of the subject invention is substituted in an equivalent amount for the U-57,930E or U-60,970E shown in the example to provide therapeutic properties.

Similarly, each of the above free base compounds can be used in the form of a pharmaceutically (or pharmacologically) acceptable acid addition salt, e.g., hydrochloride, sulfate, nitrate, phosphate, citrate, lactate, acetate, tartrate and succinate.

Further, the 2-phosphate and/or 2-palmitate of each of the above antibacterially-active invention compounds can be substituted as the active ingredient to provide compositions having therapeutic properties.

I claim:

1. A compound of the formula

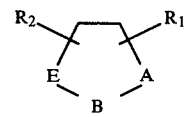

wherein A, B and E are selected from the group consisting of nitrogen, oxygen, sulfur and $CR_1R_1$; wherein $R_1$ is selected from the group consisting of hydrogen, alkyl and substituted alkyl wherein the alkyl portion is from 1 to 8 carbon atoms, inclusive, and isomeric forms thereof, cycloalkyl and substituted cycloalkyl, substituted oxygen, substituted nitrogen, halogen, phenyl, and substituted phenyl, —$(CH_2)_n$—OH, —$(CH_2)_n$—$NR_4R_5$, and isomeric forms thereof, wherein n is an integer of from 1 to 8, inclusive, $R_4$ and $R_5$ are H or alkyl of from 1 to 8 carbon atoms, inclusive, and isomeric forms thereof; wherein $R_2$ is

and X is the amino function of a compound selected from the group 7(R)-hydroxy-methyl 1-thio-α-lincosaminide, 7(S)-hydroxy-methyl 1-thio-α-lincosaminide, 7(S)-halo-methyl 1-thio-α-lincosaminide, 7(R)-halo-methyl 1-thio-α-lincosaminide, 7(S)-methoxy-methyl 1-thio-α-lincosaminide, 7-deoxy-7(S)-(methylthio)-methyl 1-thio-α-lincosaminide, 7-deoxy-7(S)-(2-hydroxyethylthio)-methyl 1-thio-α-lincosaminide and 7-deoxy-7(S)-(3-hydroxypropylthio)-methyl 1-thio-α-lincosaminide; $R_1$ and $R_2$ can be attached to any ring carbon or nitrogen atom; $R_1$ can be multiply attached to any ring carbon atom, and the pharmaceutically acceptable acid addition salts thereof.

2. A compound, according to claim 1, of the formula

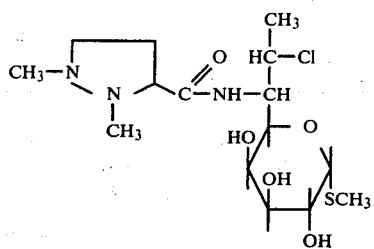

and the pharmaceutically acceptable acid-addition salts thereof.

3. The 2-palmitate of the compounds defined in claim 1.

* * * * *